United States Patent [19]
Eno

[11] Patent Number: 6,113,823
[45] Date of Patent: Sep. 5, 2000

[54] PYROLYTIC CARBON TRANSMYOCARDIAL IMPLANT

[75] Inventor: Robert A. Eno, Plymouth, Minn.

[73] Assignee: Heartstent Corporation, St. Paul, Minn.

[21] Appl. No.: 09/094,136

[22] Filed: Jun. 9, 1998

[51] Int. Cl.[7] .......................... B29C 33/48; B29C 41/10; B29C 41/42
[52] U.S. Cl. .................. 264/81; 264/159; 264/162; 264/163; 264/219; 264/221; 264/317; 264/DIG. 51; 264/85; 604/8; 623/901
[58] Field of Search .................. 264/81, 85, 157, 264/162, 163, 219, 221, 317, DIG. 51, 159; 604/8; 623/901, 1, 2, 11, 12

[56] References Cited

U.S. PATENT DOCUMENTS

| | | | |
|---|---|---|---|
| 3,977,896 | 8/1976 | Bokros et al. | 427/213 |
| 4,015,601 | 4/1977 | Bokros et al. | 128/214 R |
| 4,349,498 | 9/1982 | Ellis et al. | 264/81 |
| 4,854,846 | 8/1989 | Oglesby | 425/391 |
| 5,229,061 | 7/1993 | Van Dyke et al. | 264/303 |
| 5,262,104 | 11/1993 | Schwartz | 264/81 |
| 5,755,682 | 5/1998 | Knudson et al. | 604/8 |
| 5,935,506 | 8/1999 | Schmitz et al. | 264/400 |

FOREIGN PATENT DOCUMENTS

| | | |
|---|---|---|
| 98/06356 | 2/1988 | WIPO . |
| 98/08456 | 3/1998 | WIPO . |

OTHER PUBLICATIONS

Bokros, J. C., "Carbon Biomedical Devices," *Carbon*, 15:355–371 (1977).

Bokros, J. C. et al., "Control of Structure of Carbon for Use in Bioengineering," *Gulf Oil Corporation*, pp. 103–171 (Undated).

Bokros, J. C. et al., "Correlations between Blood Compatibility and Heparin Adsorptivity for an Impermeable Isotropic Pyrolytic Carbon," *J. Biomed Mater. Res.*, 3:497–528 (1969).

Bokros, J. C. et al., "Heparin Sorptivity and Blood Compatibility of Carbon Surfaces," *J. Biomed Mater. Res.*, 4:145–187 (1970).

Bokros, J. C. et al., "Protheses made of carbon," *Chemtech*, pp. 40–49 (Jan. 1977).

Schoen, F. J., "Carbons in Heart Valve Prostheses: Foundations and Clinical Performance," *Biocompatible Polymers, Metals, and Composites*, pp. 239–261 (1983).

*Primary Examiner*—Jill L. Heitbrink
*Assistant Examiner*—Michael I. Poe
*Attorney, Agent, or Firm*—Merchant & Gould P.C.

[57] ABSTRACT

A bypass conduit having a desired hollow internal geometry for defining a bounded blood flow path from an open first end positioned in a heart chamber and an open second end connected to a lumen of a coronary vessel is made by forming a master having an external surface with an external geometry complementary to the desired internal geometry of the conduit. The external surface of the master is coated with pyrolytic carbon to define a pyrolytic carbon conduit of pyrolytic carbon bonded to the external surface of the master and with the pyrolytic carbon having an internal surface with a conduit geometry complementary to the external geometry of the master. The master is removed from the pyrolytic carbon conduit.

6 Claims, 2 Drawing Sheets

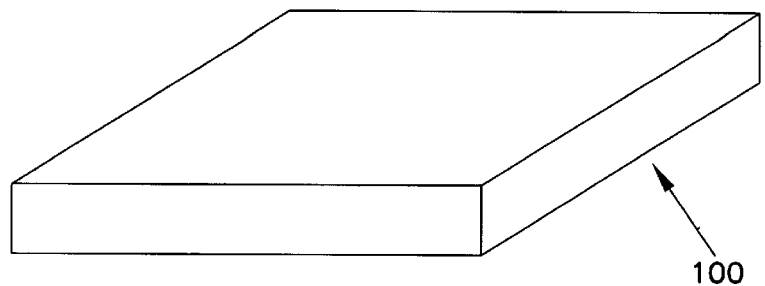
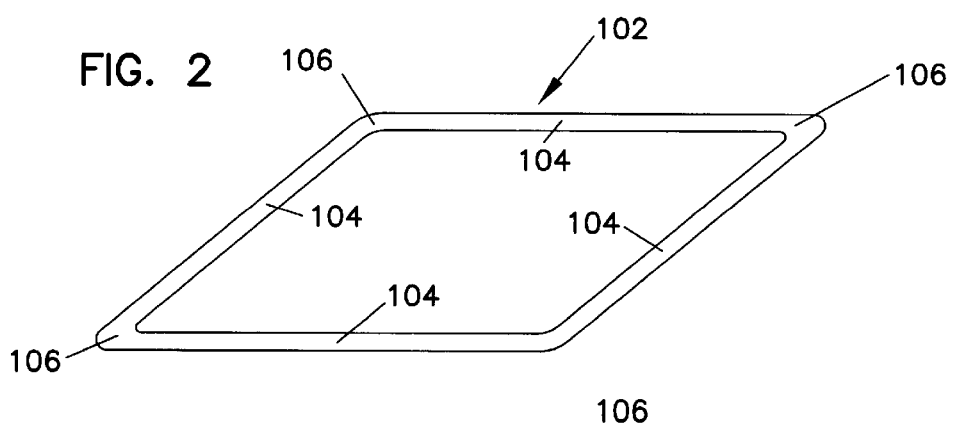
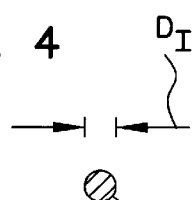
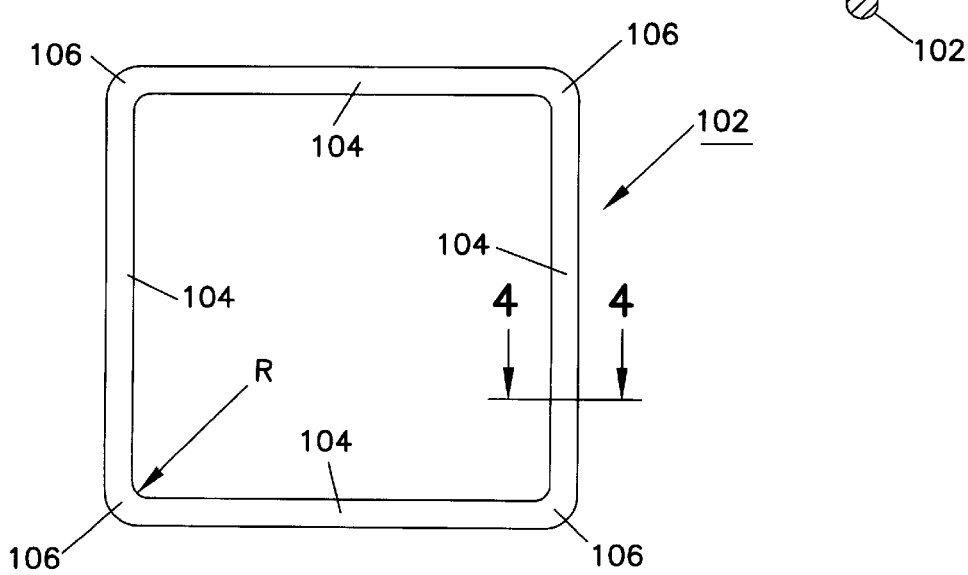

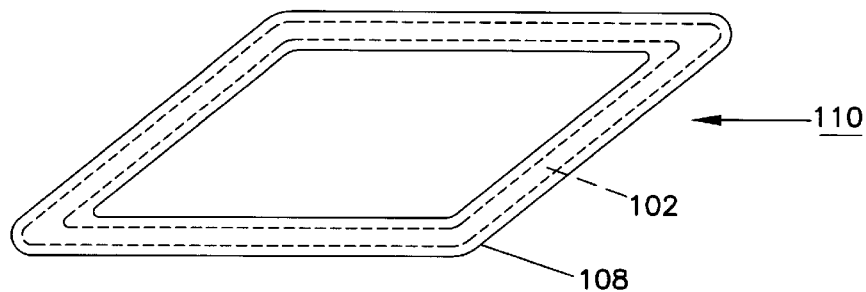
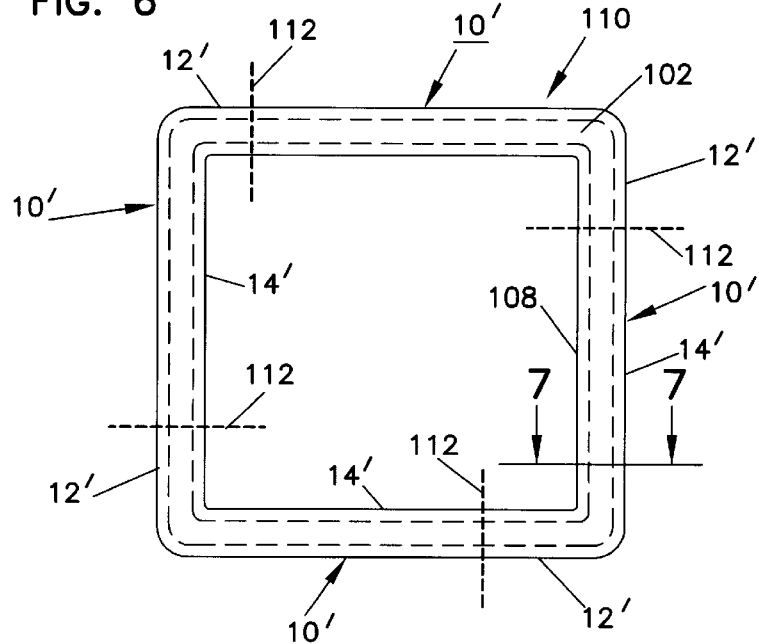
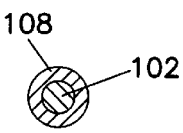
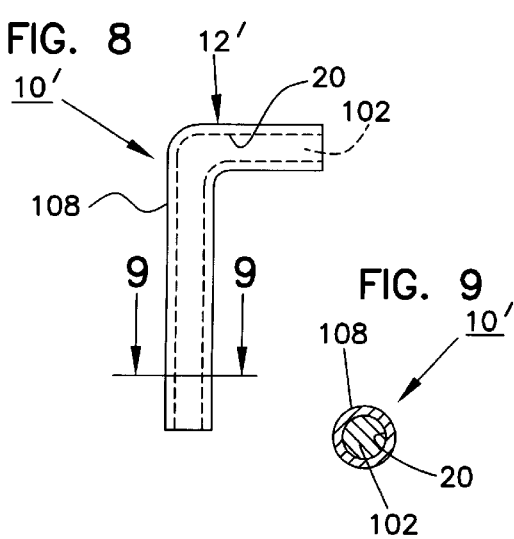
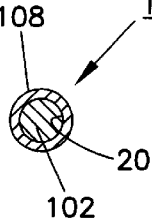
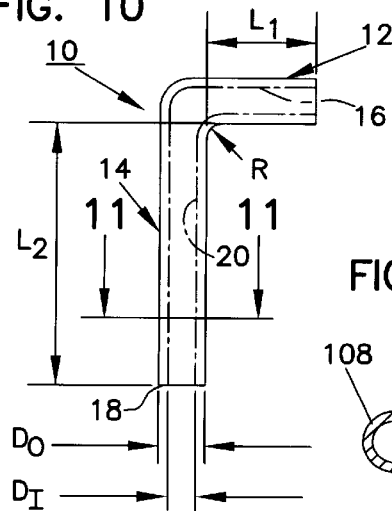
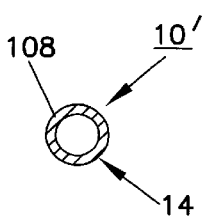

PYROLYTIC CARBON TRANSMYOCARDIAL IMPLANT

BACKGROUND OF THE INVENTION

1. Field of the Invention

This invention pertains to an implant for passing blood flow directly between a chamber of the heart and a coronary vessel. More particularly, this invention pertains to such an implant formed of pyrolytic carbon and a method of making such an implant.

2. Description of the Prior Art

Commonly assigned and co-pending U.S. patent application Ser. No. 08/882,397 filed Jun. 25, 1997, now U.S. Pat. No. 5,944,019, entitled "Method and Apparatus for Performing Coronary Bypass Surgery", and filed in the name of inventors Mark B. Knudson and William L. Giese (also filed as PCT application Ser. No. PCT/US97/13980 published Feb. 25, 1998), teaches an implant for defining a blood flow conduit directly from a chamber of the heart to a lumen of a coronary vessel. An embodiment disclosed in the aforementioned application teaches an L-shaped implant in the form of a rigid conduit having one leg sized to be received within a lumen of a coronary artery and a second leg sized to pass through the myocardium and extend into the left ventricle of the heart. As disclosed in the above-referenced application, the conduit is rigid and remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 08/944,313 filed Oct. 6, 1997, now U.S. Pat. No. 5,984,956, entitled "Transmyocardial Implant", and filed in the name of inventors Katherine S. Tweden, Guy P. Vanney and Thomas L. Odland, teaches an implant such as that shown in the aforementioned '397 application with an enhanced fixation structure. The enhanced fixation structure includes a fabric surrounding at least a portion of the conduit to facilitate tissue growth on the exterior of the implant.

Implants such as those shown in the aforementioned applications include a portion to be placed within a coronary vessel and a portion to be placed within the myocardium. Such implants may be made of titanium. Titanium has a long history for use as an implant material in contact with blood. For example, titanium is used as a material in heart valves because it is thrombo-resistant.

Another desirable material for use in blood-contacting implants is pyrolytic carbon. Long used in heart valves, pyrolytic carbon is biocompatible and thrombo-resistant.

In the heart valve industry, pyrolytic carbon is used to coat the external, blood contacting surfaces component parts. For example, a part, such as a valve leaflet, is first formed of a substrate material with dimensions smaller than the desired part but conforming in geometry to the desired part. A common substrate material is graphite because pyrolytic carbon adheres to graphite and graphite is resistant to thermal expansion and can tolerate the extreme temperatures experienced when applying pyrolytic carbon.

The graphite substrate is placed in a fluidized bed reactor with a reaction zone having temperatures of about 1,300° C. Propane gas is used as a carbon source. The carbon is deposited on the external surface of the part as pyrolytic carbon. The coating continues for a time selected to achieve a desired thickness of the pyrolytic carbon so that the final part has a size approximate to the desired size of the part. The pyrolytic carbon layer assumes the geometry of the external surface of the graphite substrate. If necessary the pyrolytic carbon can be machined. For certain applications, it is desired for the pyrolytic carbon to be alloyed with silicon to enhance wear resistance. In such cases, methyltrichlorosilane is added to the reactor as a silicon source during the fluidized bed reaction.

The afore-said applications disclose the desirability of a pyrolytic or pyrolytic-coated titanium implant. However, for use as such an implant, the interior surface of such an implant should be pyrolytic carbon as opposed to the external surfaces of valve components. The afore-mentioned process for coating external surfaces with pyrolytic carbon do not suggest how to form an implant with an internal surface of pyrolytic carbon. Further, a typical such implant has a curved interior surface further frustrating attempts to fabricate or coat the implant with pyrolytic carbon. Also, the long, narrow (i.e., the diameter is less than the length) blood flow path frustrates attempts to so fabricate or coat.

SUMMARY OF THE INVENTION

According to a preferred embodiment of the present invention, a method is disclosed for forming a by-pass conduit having a desired hollow internal geometry for defining a bounded blood flow path from an open first end positioned in a heart chamber and an open second end connected to a lumen of a coronary vessel. The method comprises forming a master having an external surface with an external geometry complementary to the desired internal geometry of the conduit. The external surface of the master is coated with pyrolytic carbon to define a pyrolytic carbon conduit of pyrolytic carbon bonded to the external surface of the master and with the pyrolytic carbon having an internal surface with a conduit geometry complementary to the external geometry of the master. The master is removed from the pyrolytic carbon conduit.

BRIEF DESCRIPTION OF THE DRAWINGS

FIG. 1 is a perspective view of a graphite block for use in forming a master according to the method of the present invention;

FIG. 2 is a perspective view of a master ring machined from the block of FIG. 1;

FIG. 3 is a top plan view of the master ring of FIG. 2;

FIG. 4 is a view taken along line 4—4 in FIG. 3;

FIG. 5 is a perspective view of the master ring of FIG. 2 coated with pyrolytic carbon and showing an external surface of the master in phantom lines;

FIG. 6 is a top plan view of the coated master ring of FIG. 5

FIG. 7 is a view taken along line 7—7 in FIG. 6;

FIG. 8 is an elevation side view of one of four graphite filled conduits formed by splitting the coated master ring of FIG. 5;

FIG. 9 is a view taken along line 9—9 in FIG. 8;

FIG. 10 is an elevation side view of the conduit of FIG. 8 with an internal surface shown in dot-and-dash phantom lines defining an internal bore; and FIG. 11 is a view taken along line 11—11 in FIG. 10.

IV. DESCRIPTION OF THE PREFERRED EMBODIMENT

Referring now to the several drawing figures in which identical elements are numbered identically throughout, a description of a preferred embodiment will now be provided.

The present invention is directed toward a rigid, hollow conduit for providing a blood flow path between a heart chamber (e.g., a left ventricle) and a coronary vessel (e.g., a coronary artery). With initial reference to FIG. 10, a finished implant or conduit 10 is shown in the form of an L-shaped rigid tube. In a process as will be described, the conduit 10 is formed of pyrolytic carbon. The pyrolytic carbon is rigid in order to withstand contraction forces of the myocardium, as will be described.

By way of non-limiting example, the conduit 10 has an outside diameter $D_O$ of about 1.5 to 3.5 millimeters (to fit into coronary vessels with similarly sized lumens) and an internal diameter $D_I$ of about 1.0 to 3.0 millimeters to provide a wall thickness of about 0.5 millimeters.

The tube 10 has a first portion 12 sized to be received within the lumen of a coronary vessel such as the lumen of a coronary artery. The conduit 10 has a second portion 14 extending at a right angle to the axis of portion 12. The second portion 14 is sized to extend from the coronary artery directly through the myocardium and protrude into the left ventricle of a patient's heart. The second portion 14 is sized to have a length sufficient for the portion 14 to protrude into the left ventricle. Again, by way of non-limiting example, the length $L_1$ of first portion 12 is about 10 millimeters and the length $L_2$ of second portion 14 is about 30 millimeters. The actual length and diameters of the portions 12, 14 are selected to fit into an artery distal to an occlusion and penetrate through the myocardium into the left ventricle as described in the afore-mentioned commonly assigned patent applications. To provide laminar blood flow, a radius R of equal to the diameter $D_I$ is provided between the portions 12, 14.

The first portion 12 has a first opening 16 and the second portion 14 has a second opening 18 in communication with an interior blood flow path 20 of the implant 10. Therefore, blood can freely flow through the implant 10 between the left ventricle and the lumen of the coronary artery. The blood flow path 20 is an elongated and completely enclosed (but for openings 16, 18) narrow, tubular pathway having a length equal to the combined lengths of the portions 12, 14 and a diameter $D_I$ and a bend of radius R between the portions 12, 14.

As disclosed in the afore-mentioned U.S. patent application Ser. No. 08/944,313, the implant 10 can be provided with a fabric cuff (not shown in the present application) on the exterior of portion 14 to facilitate myocardial tissue in-growth. Although not shown in FIG. 10, the exterior of the implant 10 may be provided with annular grooves to receive sutures for holding such a cuff in place as taught in the '313 application.

As mentioned, the implant 10 is preferably formed of pyrolytic carbon in order to resist tissue growth and thrombosis on the surfaces of the conduit 10. Pyrolytic carbon is a preferred material due its long-term use in the cardiovascular industry. Further, it is sufficiently rigid to withstand deformation forces caused by contraction of the myocardium to avoid deformation of the tube 10 so that the tube 10 remains open during both diastole and systole.

Unfortunately, pyrolytic carbon has proven difficult to form in a bent tube as required for implant 10. Also, it is difficult to coat a titanium or other bent implant with pyrolytic carbon. The present invention is directed to a method for making the implant of pyrolytic carbon.

The present invention utilizes a master having an external shape corresponding to a desired internal shape of the implant. The master is formed from a block 100 of graphite as illustrate in FIG. 1. Graphite is used as a master material because pyrolytic carbon adheres to graphite. Graphite can withstand the extreme temperatures (in excess of 1,300° C.) present in a fluidized bed reactor. Also, graphite is strong enough to be machined to a desired state yet soft enough to permit removal from a finished part as will be described. In use in fluidized bed reactors to act as a substrate for pyrolytic carbon for heart valve parts, graphite has proven itself able to withstand the stress of a fluidized reactor. Graphite exhibits low thermal expansion over the temperature range in the coating process. By way of non-limiting example, a presently preferred graphite is product designation AXF-5Q from POCO Graphite, Inc., Decatur, Texas.

The graphite block 100 is machined into a generally square-shaped master ring 102 as illustrated in FIGS. 2–4. For reasons that will be described, the master ring 102 is a square shaped ring from which four implants can be formed.

Each straight length 104 of the square master ring 102 is equal to the sum of the interiors of the portions 12, 14 of a finished implant 10. Each corner 106 of the square master ring 102 is provided with the same radius as the radius of the finished implant 10. The diameter $D_I$ of the master ring 102 is the same as the interior diameter of the finished implant 10. Therefore, the master ring 102 has the same external dimensions and geometry as four interior blood flow paths 20 of a finished implant 10 joined end-to-end to form a square ring.

Preferably, the ring 102 is polished as smooth as possible (e.g., less than 1 micron polish) so that the formed internal surface 20 of the finished implant 10 will be a smooth as possible to avoid or reduce polishing of the implant 10. Polishing graphite is well within the skill of the art.

The formed and polished ring 102 is placed within a fluidized bed reactor (not shown). Using propane gas as a carbon source, the reactor deposits a pyrolytic carbon layer 108 on the external surface of the ring 102 (FIGS. 5–7). Controlling the residence time of the ring 102 in the reactor helps control the thickness of the deposited pyrolytic carbon coating 108. The thickness of the coating 108 is substantially uniform throughout the perimeter of the ring 102. In this regard, the ring 102 provides a benefit over individually forming implants 10. While possible within the scope of the present invention, such individual forming can leading to thickened areas of coating 108 at ends 16, 18. The thickening, which would require additional machining, is avoided by forming four implants 10 from a common ring 102.

While not preferred, if silicon alloyed pyrolytic carbon is desired, methyltrichlorosilane can be added to the reactor as a silicon source as is conventional. It will be appreciated that the formation of a pyrolytic carbon layer on an external surface of graphite in a fluidized bed reactor is well known in the art and is not separately described.

During the fluidized bed reaction, the ring 102 is coated with a pyrolytic carbon 108 to a desired thickness to form an assembly 110 of a coated ring. Due to the uniformity of coating thickness, the external geometry of the coating 108 generally conforms with the external geometry of the master ring 102.

If desired, the external geometry of the pyrolytic carbon coating 108 can be machined to any desired shape. The coated ring 110 is then split at the severance locations 112 shown in FIG. 6. The splitting forms four separate combinations 10' (FIGS. 8 and 9) having two lengths 12', 14' joined at 90°. The pyrolytic coating 108 of each of the combinations 10' has the identical geometry as the finished implant 10 with an internal bore 20 filled with a portion of the graphite ring 102.

The soft graphite 102 is removed by a vapor jet operation. Apparatus for performing such an operation are commercially available. Compressed air with an entrained abrasive (e.g., sodium bicarbonate) is ejected from a nozzle in a high velocity, narrow stream. The compressed air with entrained sodium bicarbonate (or other soft abrasive) removes the graphite 102 without abrading the pyrolytic carbon coating 108.

With the graphite 102 removed, a completed implant 10 is formed (FIGS. 10 and 11). The implant 10 can be polished externally and internally if desired. Internal polishing may include a soft cloth rope or other material as a carrier of abrasive medium advanced through the bore 20. Alternatively, a flow of abrasive slurry can be passed through the bore 20.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims which are appended hereto. For example, in the event that the internal bore 20 of the implant 10 is to have a different internal geometry, the external geometry of the ring 102 can be machined to any configuration or shape to present a geometry complementary to the desired geometry of the internal surface 20 of the implant 10. For example, if a non-circular interior bore 20 is desired, the master ring 102 can be machined with a complementary shaped non-circular exterior. Similarly, if the finished implant bore 20 is desired (e.g., for reasons of hemodynamics) to have a non-uniform cross-section throughout its length, the master ring 102 can be machined with a complementary shaped exterior of non-uniform cross-section.

What is claimed is:

1. A method for forming a plurality of by-pass conduits, each conduit having a desired hollow internal geometry for defining a bounded blood flow path from an open first end positioned in a heart chamber and an open second end connected to a lumen of a coronary vessel, the bounded blood flow path being a narrow tubular pathway which is elongated and is completely enclosed but for the open first end and the open second end, and having a bend, the method comprising:

forming from master material a master having an external surface with an external geometry complementary to the desired internal geometry and having bends corresponding to the bends of the bounded blood flow paths, the master being formed in a continuous ring of master material sized to form a plurality of the conduits;

coating the external surface of the entire ring with pyrolytic carbon to define a pyrolytic carbon conduit assembly of pyrolytic carbon bonded to the external surface of the master and with the pyrolytic carbon conduit assembly having an internal surface with a conduit geometry complementary to the external geometry of the master;

splitting the pyrolytic carbon conduit assembly into a plurality of individual conduit members; and removing the master material from the individual conduit members to form a plurality of completed conduits of pyrolytic carbon with the inner carbon surface of each completed conduit defining the bounded blood flow path of each completed conduit.

2. A method according to claim 1 wherein the pyrolytic carbon is applied to the external surface in a fluidized bed reactor.

3. A method according to claim 1 wherein the master a material is selected for properties of low thermal expansion, high temperature tolerance and adherence to pyrolytic carbon.

4. A method according to claim 3 wherein the master material is graphite.

5. A method according to claim 4 wherein the master is machined to form the external surface.

6. A method according to claim 5 wherein the external surface is polished prior to the coating.

* * * * *